United States Patent
Xu et al.

(10) Patent No.: US 10,151,701 B2
(45) Date of Patent: Dec. 11, 2018

(54) SPECTRALLY RESOLVED SUPER-RESOLUTION MICROSCOPY AND ULTRAHIGH-THROUGHPUT SINGLE-MOLECULE SPECTROSCOPY

(71) Applicant: THE REGENTS OF THE UNIVERSITY OF CALIFORNIA, Oakland, CA (US)

(72) Inventors: Ke Xu, Kensington, CA (US); Zhengyang Zhang, Albany, CA (US); Samuel J. Kenny, Berkeley, CA (US); Margaret Hauser, Berkeley, CA (US); Wan Li, Kensington, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/892,575

(22) Filed: Feb. 9, 2018

(65) Prior Publication Data
US 2018/0275060 A1    Sep. 27, 2018

Related U.S. Application Data

(63) Continuation of application No. PCT/US2016/046821, filed on Aug. 12, 2016.
(Continued)

(51) Int. Cl.
G01N 21/64 (2006.01)
G01J 3/44 (2006.01)
G02B 21/06 (2006.01)
G02B 27/58 (2006.01)
G02B 21/36 (2006.01)
G02B 21/16 (2006.01)

(52) U.S. Cl.
CPC ........ *G01N 21/6458* (2013.01); *G01J 3/4406* (2013.01); *G01N 21/6428* (2013.01); *G02B 21/16* (2013.01); *G02B 21/367* (2013.01); *G02B 27/58* (2013.01); *G01N 2021/6421* (2013.01); *G01N 2021/6439* (2013.01)

(58) Field of Classification Search
CPC .......... G01J 3/4406; G01N 2021/6421; G01N 2021/6439; G01N 21/6428; G01N 21/6458; G02B 21/16; G02B 21/367; G02B 27/58
See application file for complete search history.

(56) References Cited

U.S. PATENT DOCUMENTS

| 2013/0027518 A1 | 1/2013 | Mackay |
| 2013/0126755 A1 | 5/2013 | Kemnitz |
| 2014/0333750 A1 | 11/2014 | Zhuang |

FOREIGN PATENT DOCUMENTS

WO    2016049544 A1    3/2016

OTHER PUBLICATIONS

ISA/US, United States Patent and Trademark Office, International Search Report and Written Opinion dated Oct. 28, 2016, related PCT international application No. PCT/US2016/046821, pp. 1-15, with claims searched, pp. 16-23.
(Continued)

*Primary Examiner* — Mark R Gaworecki
(74) *Attorney, Agent, or Firm* — O'Banion & Ritchey LLP; John P. O'Banion

(57) ABSTRACT

Systems and methods for spectrally resolved super-resolution microscopy (SRM) and ultrahigh-throughput single-molecule spectroscopy to synchronously and rapidly measure the fluorescence spectra and positions of millions of single molecules in dense samples.

38 Claims, 8 Drawing Sheets

Related U.S. Application Data

(60) Provisional application No. 62/204,049, filed on Aug. 12, 2015.

(56) References Cited

OTHER PUBLICATIONS

Bates, Mark et al., "Stochastic Optical Reconstruction Microscopy (STORM): A Method for Superresolution Fluorescence Imaging", Cold Spring Harb Protoc; 2013; doi:10.1101/pdb.top074143, downloaded from http://cshprotocols.cshlp.org/ on Sep. 30, 2016, pp. 498-520 (24 pages total).

Michalet, Xavier et al., "Ultrahigh-Resolution Colocalization of Spectrally Separable Point-Like Fluorescent Probes", Methods 25, 87-102 (2001), 17 pages total.

Zhang, Zhengyang et al., "Ultrahigh-throughput single-molecule spectroscopy and spectrally resolved super-resolution microscopy", Brief Communications, Nature Methods, Advance Online Publication, doi:10.1038/nmethod.3528, published online Aug. 17, 2015, pp. 1-6.

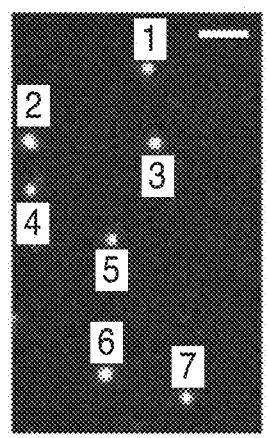
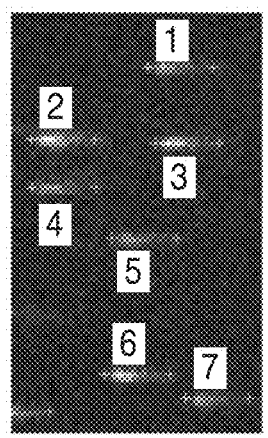
FIG. 4A  FIG. 4B
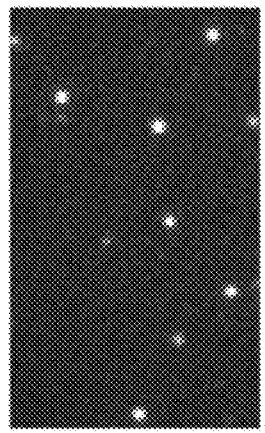
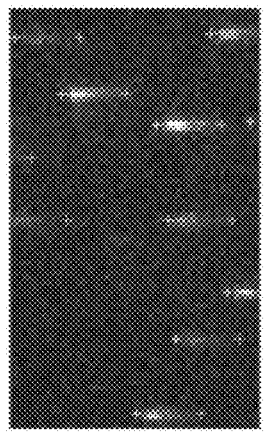
FIG. 5A  FIG. 5B

SPECTRALLY RESOLVED SUPER-RESOLUTION MICROSCOPY AND ULTRAHIGH-THROUGHPUT SINGLE-MOLECULE SPECTROSCOPY

CROSS-REFERENCE TO RELATED APPLICATIONS

This application is a 35 U.S.C. § 111(a) continuation of PCT international application number PCT/US2016/046821 filed on Aug. 12, 2016, incorporated herein by reference in its entirety, which claims priority to, and the benefit of, U.S. provisional patent application Ser. No. 62/204,049 filed on Aug. 12, 2015, incorporated herein by reference in its entirety. Priority is claimed to each of the foregoing applications.

The above-referenced PCT international application was published as PCT International Publication No. WO 2017/027818 on Feb. 16, 2017, which publication is incorporated herein by reference in its entirety.

STATEMENT REGARDING FEDERALLY SPONSORED RESEARCH OR DEVELOPMENT

This invention was made with government support under DE-AC02-05CH11231, awarded by the U.S. Department of Energy. The government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to super-resolution microscopy, and more particularly to spectrally-resolved stochastic optical reconstruction microscopy.

2. Background Discussion

Emerging super-resolution microscopy (SRM) methods offer outstanding spatial resolution but no spectral information. As a result, high-quality multicolor 3D SRM remains a challenge, and issues like heavy color crosstalk, compromised image quality, and difficulties in aligning the 3D coordinates of different color channels. Meanwhile, current, scanning-based single-spot approaches for single-molecule spectrum measurement are limited by low-throughput, low spatial resolution, and are unfeasible for densely labeled (biological) samples.

Traditional methods to obtain the spectra of single molecules follow the approach of a conventional spectrometer, where a combination of confined illumination (e.g., a scanning tip or focused laser beam) and confined detection (e.g., pinhole aperture in a co focal microscope) are used to obtain locally confined fluorescence of the sample for dispersion into a spectrum in 1D. Scanning of the sample is then used to visit different positions and thus different molecules. Thus, spatial sparseness of fluorescent molecules is needed to avoid overlap between the dispersed spectra. Such an approach is very low in throughput and takes minutes to scan through a 2D area.

BRIEF SUMMARY

An aspect of the present technology is spectrally resolved super-resolution microscopy (SRM) and ultrahigh-throughput single-molecule spectroscopy that is configured to synchronously measure the fluorescence spectra and positions of millions of single molecules in dense samples over a short period of time.

With use of a wide-field scheme for spectral measurement and photoswitching, the fluorescence spectra and positions of ~$10^6$ single molecules were synchronously obtained in labeled cells in minutes, allowing spectrally resolved, "true-color" super-resolution microscopy. The systems and methods of the present technology, called Spectrally-Resolved Stochastic Optical Reconstruction Microscopy (SR-STORM), were able to achieve crosstalk-free three-dimensional (3D) imaging for four dyes 10 nm apart in emission spectrum. Excellent resolution was obtained for every channel, and 3D localizations of all molecules were automatically aligned within one imaging path.

The systems and methods of the present description employ mechanisms to first switch most of the molecules into a non-emitting dark state and only allowing a small, random subset of the molecules to be in the fluorescent state at any given instance, so that at any given instance, fluorescence of the remaining, sparsely distributed subset of emitting molecules can be dispersed into non-overlapping spectra in wide-field and recorded with a camera. Stochastic switching of molecules between the dark and fluorescent states then allows for the synchronous spectrum measurement and super-localization of millions of single molecules within minutes.

In one embodiment, fluorescence switching is achieved through controlled photoswitching in combination with recording the position of single molecules, where the spectrum of each molecule is recorded in the wide-field.

By controlling the fluorescence switching off-rate to match the frame rate of the EM-CCD camera (100+ FPS), and the on-rate to achieve an optimal density of emitting molecules (tens to hundreds of molecules per frame), the systems and methods of the present technology acquire the fluorescence spectra (as well as localizations) of single molecules with an ultrahigh throughput of tens of thousands of molecules per second, or millions of molecules in minutes.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 4A and FIG. 4B show actual data obtained from a dual-objective system as detailed in FIG. 1.

FIG. 5A and FIG. 5B show images/spectra from the same setup as FIG. 4A and FIG. 4B, but for another frame that is 1 s later.

DETAILED DESCRIPTION

Figure 1:
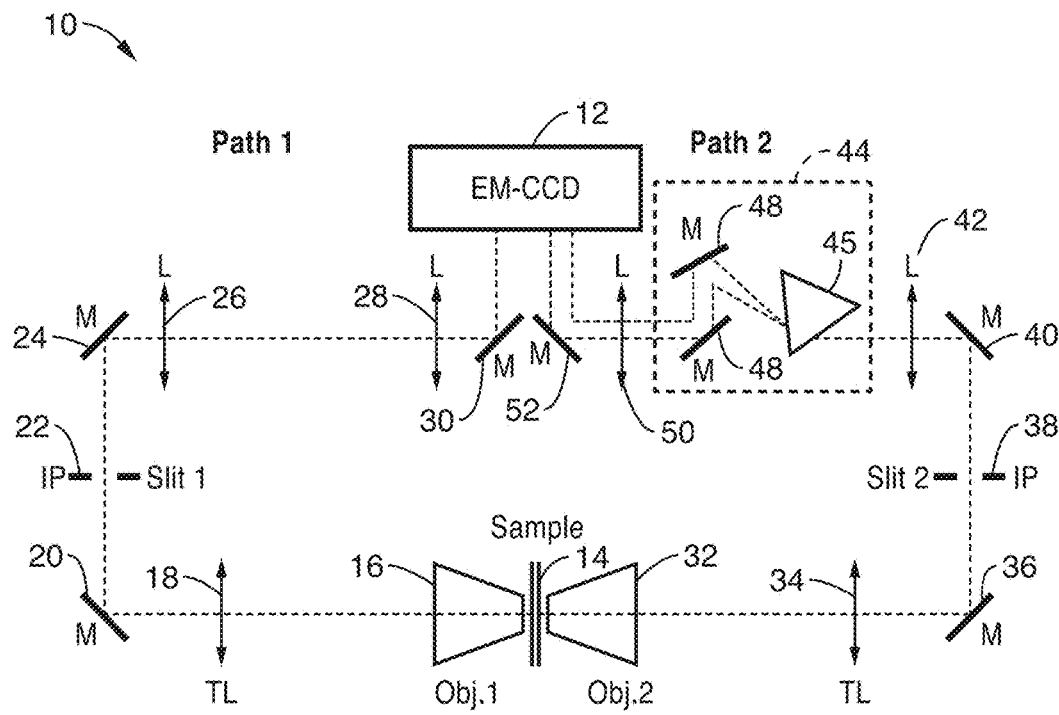
FIG. 1 shows an imaging system configuration for concurrent spectral measurement and localization of single molecules in wide-field using two opposing objective lenses.

1. High-Throughput Dispersion of Single-Molecule Spectra in Wide-Field

A premise of the present technology is that a single fluorescent molecule is, in itself, a self-confined point source, and so in principle its emitted fluorescence may be dispersed into a spectrum in wide-field without spatial confinement in illumination or detection. For multiple molecules in the same sample, the spectrum of each molecule is simultaneously recorded in wide-field, provided that the fluorophores are sparsely distributed in space to avoid overlapping of signal.

By placing a dispersing prism at the Fourier plane between the two relay lenses in the system, the fluorescence of the sample successfully disperses into spectra along x in the wide-field. A particular advantage of this wide-field spectroscopy approach is high throughput. Using a camera, the spectra of tens to hundreds of point sources (single molecules) are simultaneously collected in the wide-field in a snapshot. All pixels of the camera are utilized. Thus, single-molecule spectral measurement of the entire field only takes <10 ms. In comparison, the traditional single-point approach necessitates point-by-point scanning of every pixel, and so the required time to sample a 2D field increases drastically (minutes).

2. Fluorescence Switching for Molecular Sparseness and Ultrahigh-Throughput Spectral Measurement The systems and methods of the embodiments disclosed herein employ mechanisms to first switch most of the molecules into a non-emitting dark state, thereby only allowing a small, random subset of the molecules to be in the fluorescent state at any given instance. Accordingly, any given instance, fluorescence of the remaining sparsely distributed subset of emitting molecules can be dispersed into non-overlapping spectra in wide-field. Stochastic switching of molecules between the dark and fluorescent states then allows for the synchronous spectrum measurement and localization of millions of single molecules within minutes.

A preferred approach to achieve such fluorescence switching is through controlled photoswitching, e.g. the use of photoswitching in combination with recording the position of single molecules. The systems and methods of the present description record the spectrum of each molecule in the wide-field. Besides photoswitching, the systems and methods detailed herein may also be combined with other mechanisms to achieve fluorophore sparseness, e.g., transient binding of molecules and the in situ production of fluorescent molecules through reaction.

Through controlling the fluorescence switching off-rate to match the frame rate of the EM-CCD camera (100+ FPS), and the on-rate to achieve an optimal density of emitting molecules (tens to hundreds of molecules per frame), the system and method of the present description acquire the fluorescence spectra (as well as localizations) of single molecules with an ultrahigh throughput of tens of thousands of molecules per second, or millions of molecules in minutes. Fluorescence switching and controlled photoswitching may be implemented as part of application programming or software instructions, as detailed further below.

3. Concurrent Localization and Spectral Measurement of Single Molecules in Wide-Field In the wide-field spectroscopy scheme of the present technology, the spatial and spectral information of a randomly located single molecule become coupled due to the spreading of the spectrum out as a function of space on the camera. Thus, by obtaining the dispersed single-molecule spectra alone (e.g., see FIG. 3B below), one could not determine the wavelength extent of each spectrum: a red molecule may appear identical to a blue molecule that physically locates further to the right on the camera.

To decouple the two, the systems and methods of the present description concurrently acquire the non-dispersed images and dispersed spectra of the same single molecules in the wide-field.

Figure 2:
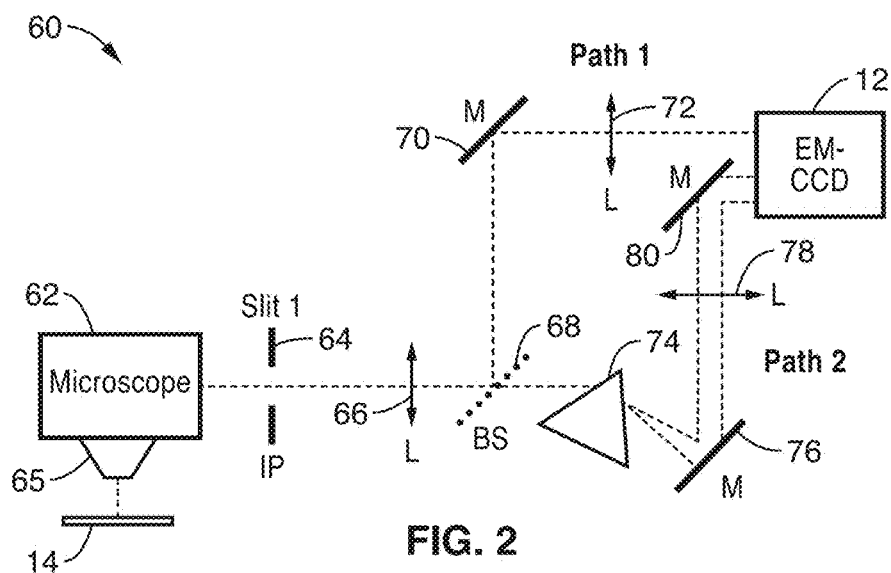
FIG. 2 shows an imaging system configured to achieve concurrent spectral measurement and localization of single molecules in wide-field using a commercial microscope that has one objective lens.

FIG. 1 and FIG. 2 show two alternative implementations to achieve concurrent spectral measurement and localization of single molecules in wide-field.

FIG. 1 shows an imaging system 10 configuration for concurrent spectral measurement and localization of single molecules in wide-field using two opposing objective lenses 16 and 32. In the imaging system 10, a second objective lens 32 is positioned at the back of the sample 14 opposite the first objective lens 16, so that two matching images are first obtained for every single molecule through the two opposing objective lenses 16 and 32 (e.g. through Path 1 and Path 2). Path 1 is used to obtain the position of each molecule, while the signal in Path 2 is dispersed to generate spectra of the same molecules in wide-field.

Path 1 comprises a tube lens (TL) 18 and mirror (M) 20 disposed between first objective 16 and the intermediate image plane (IP) 22 (Slit 1) of the objective lens 16. Path 1 further includes lenses (L) 26 and 28 disposed between mirrors 24 and 30 prior to reaching CCD 12.

Path 2 comprises a tube lens (TL) 34 and mirror (M) 36 disposed between second objective lens 32 and the intermediate image plane (IP) 38 (Slit 2) of the objective lens 32. The intermediate image of single molecules was collimated by the first relay lens 42 and mirror 40, and the resultant parallel light was dispersed by the prism 45 before being focused by the second relay lens 50 and mirror 52 to form spectra of single molecules on the EM-CCD 12. Two mirrors 48 were used to steer the light split from prism 45 so that image positions in the image mode and in the spectrum mode (see FIG. 4A through FIG. 5B below) roughly matched each other (e.g. for a laser wavelength at 647 nm). To facilitate alignment and calibration, the prism 45 and mirrors 48 were mounted on a motorized linear translation stage 44 (e.g., PT1-Z8, Thorlabs) so they can be readily translated in and out to switch Path 2 between the image mode and the spectrum mode.

In one exemplary embodiment, objectives 16, 32 comprise two infinity-corrected microscope objectives (e.g. Olympus Super Apochromat UPLSAPO 100×, oil immersion, numerical aperture 1.40, default tube lens f=180 mm), and were placed opposite each other and aligned to focus on the same spot of the sample 14. Two piezoelectric actuators (DRV120 and DRV517, Thorlabs, not shown) were used to control the axial positions of the sample 14 and first objective 16 with nanometer precision.

For clarity, illumination optics are not shown in either of the configurations detailed in FIG. 1 and FIG. 2. However, a light source, such as lasers (not shown) at 647 nm (MPB Communications), 560 nm (MPB Communications), and 488 nm (Coherent) were coupled into an optical fiber (not shown) after an acousto-optic tunable filter (not shown) and then introduced into the sample 14 through the back focal plane of the first objective 16 using a multiband dichroic mirror (e.g. Di01-R405/488/561/635, Semrock). Using a translation stage (not shown), the laser beams were shifted toward the edge of the objective 16 so that emerging light reached the sample 14 at incidence angles slightly smaller than the critical angle of the glass-water interface. For the spectrum mode of Path 2, prism 45 comprised an equilateral calcium fluoride ($CaF_2$) prism (e.g. PS863, Thorlabs) placed at the Fourier plane between the two relay lenses 50, 42 at the angle of minimum deviation (~0.55 rad).

The fluorescence emission collected by the first objective 16 was focused by an achromatic lens with f=200 mm, resulting in an intermediate image at Slit 1 (22) with an effective magnification of ~111×. For 3D imaging, an f=1000 mm cylindrical lens 18 (e.g. LJ1516RM-B, Thorlabs) was placed before Slit 1 (22) to introduce astigmatism into the obtained single-molecule images.

The fluorescence emission collected by the second objective 32 was filtered by a multi-notch filter (ZET405/488/561/640m, Chroma, not shown), and focused by an achromatic lens with f=150 mm, thus resulting in an intermediate image at Slit 2 (38) with an effective magnification of ~83×. The two intermediate images formed through Path 1 and Path 2 were cropped by Slit 1 (22) and Slit 2 (38) to ~8 mm in width and then separately projected onto two different areas of the same electron-multiplying charge-coupled device (EM-CCD) camera 12 (e.g. iXon Ultra 897, Andor) through two pairs of relay lenses 42/50 and 26/28. Another multi-notch filter (e.g. ZET405/488/561/640m, Chroma, not shown) was installed on the camera 12.

It is appreciated that the above detailed embodiment is provided for illustration purposes only. The components listed above are exemplary of one configuration used in the present description, but may be substituted or modified as appropriate with other options available in the art.

FIG. 2 shows an imaging system 60 configured to perform concurrent spectral measurement and localization of single molecules in wide-field using a commercial microscope 62 that has one objective lens 65. In this configuration, the fluorescence signal obtained by the objective lens 65 is split into two light paths using a beam-splitter 68, so that Path 1 and Path 2 are, respectively, used to obtain the position and spectrum of each molecule within sample 14. While a 50-50 splitting ratio works well for general applications, in practice this ratio can be readily modified by mounting multiple beam splitters (not shown) of different reflectance ratios on a filter wheel (not shown) to accommodate specific applications that emphasize either the spectrum or localization.

Path 1 of imaging system 60 further comprises a first slit 64 with an imaging plane IP between lens 66 and objective lens 65. After split by beam splitter 68, Path 1 hits mirror 70 and relay lens 72 to obtain the position of each molecule within the sample 14 on the EM-CCD 12.

For Path 2, light from prism 74 is directed via mirrors 76, 80 and lens 78 to form a spectrum of each molecule within sample 14 on the EM-CCD 12. In this embodiment no stage is needed for image/spectrum mode switching, as Path 1 is dedicate for image acquisition, and Path 2 is dedicated for spectra of the same signal from the objective 65.

4. Example 1

Figure 3A:
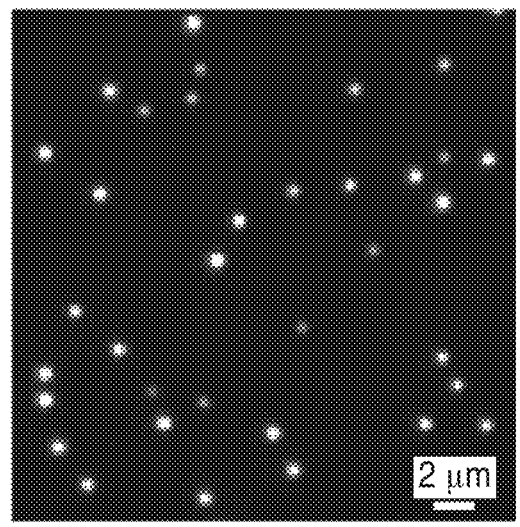
FIG. 3A shows wide-field image of 20 nm diameter fluorescent beads projected through two relay lenses.
Figure 3B:
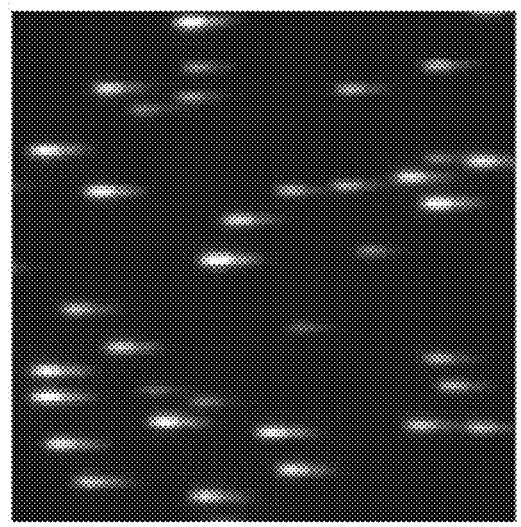
FIG. 3B shows the fluorescence of the same beads of FIG. 3A dispersed into individual spectra in the wide-field by placing a dispersing prism at the Fourier plane between relay lenses.

The principles of the present technology were demonstrated using immobilized 20 nm diameter fluorescent beads. FIG. 3A and FIG. 3B show spectral dispersion of point sources simulated via the fluorescent beads. FIG. 3A shows wide-field image of 20 nm diameter fluorescent beads projected through two relay lenses. FIG. 3B shows the fluorescence of the same beads dispersed into individual spectra in the wide-field by placing a dispersing prism at the Fourier plane between relay lenses.

Due to its small size in comparison to the wavelength of light, every bead effectively behaves as a point source, just like a single molecule, but offers more stable signal for initial tests. Individual beads thus appear as diffraction-limited spots in wide-field images (FIG. 3A). By placing a dispersing prism at the Fourier plane between the two relay lenses in the system, the fluorescence of all beads was successfully dispersed into spectra along x in the wide-field (FIG. 3B).

SR-STORM was performed on a test setup similar to the system 10 shown in FIG. 1.

Samples were prepared as follows. COS-7 and PtK2 cells (ATCC) were cultured following standard tissue culture protocols (mycoplasma regularly tested), and plated on 12 or 18 mm dia., #1.5 coverglass at ~30% confluency. After 24 h, cells were fixed using a solution of 4% paraformaldehyde in phosphate buffered saline (PBS), or 3% paraformaldehyde and 0.1% glutaraldehyde in PBS followed by two washes with 0.1% sodium borohydride in PBS. Cells were blocked and permeabilized in blocking buffer (3% bovine serum albumin with either 0.5% Triton X-100 or 0.02% saponin in PBS), followed by overnight incubation at 4° C. in primary antibody solution, washed three times, and then incubated for 45 min at room temperature in secondary antibody solution. Primary antibodies used were rat anti-alpha-tubulin (MAB1864, Millipore), chicken anti-vimentin (AB5733, Millipore), rabbit anti-Tom20 (sc-11415, Santa Cruz Biotech), mouse anti-PMP70 (SAB4200181, Sigma), and mouse anti-ATPB (ab14730, Abcam), which should label microtubules, vimentin intermediate filaments, the outer membrane of mitochondria, peroxisomes, and ATP synthase at the inner mitochondrial membrane, respectively. Secondary antibodies (Jackson ImmunoResearch) were labeled via reaction with NHS esters of selected dyes to achieve a 1:1 dye-to-antibody labeling ratio. Examined dyes were Alexa Fluor 647 and Alexa Fluor 660 (Invitrogen), Cy5 and Cy5.5 (GE healthcare), Cyanine 5 (Lumiprobe), CF647, CF660C, and CF680 (gifts from Biotium), Dyomics 634, Dyomics 649P1, and Dyomics 654 (Dyomics), and DyLight 635, DyLight 650, and DyLight 679 (Thermo Scientific). Spectrally resolved single-molecule imaging was performed in standard STORM imaging buffer that contained 5% (w/v) glucose, 100-200 mM cysteamine, 0.8 mg/mL glucose oxidase, and 40 μg/mL catalase, in Tris-HCl (pH 7.5 or pH 8.0). ~4 μL of imaging buffer was dropped at the center of a freshly-cleaned, #1.5 rectangular cover slip (24 mm by 60 mm), and the sample cover slip was mounted on the rectangular cover slip and sealed with nail polish or Cytoseal 60.

The dye-labeled cell samples were mounted on the setup and illuminated only by a 647-nm laser at an intensity of ~2 kW cm$^{-2}$, which excites the dye molecules and also photoswitches most of them into a non-emitting dark state. At any given instant, only a small, optically resolvable subset of the fluorophores in the sample were activated, by the same 647-nm laser, back to the fluorescent, emitting state. Fluorescence from the emitting single molecules was recorded through both Path 1 and Path 2 before the molecules were again photoswitched to the dark state or photobleached, and a random, new subset of the fluorophores in the sample were activated to the emitting state. The EM-CCD camera acquired images from both Paths 1 and 2 simultaneously and continuously at a frame rate of 110 Hz, which matched well with the photoswitching rate of single molecules in our experiment (on average, each detected single molecule emitted for 1.7-2.5 frames before being switched into the dark state for most of the dyes examined in this study). To map the coordinates of Path 1 and Path 2, a short movie of a few hundreds of frames were first recorded when the dispersing prism was removed from Path 2 (Image Mode), or when the dispersing prism was inserted into Path 2 (Spectrum Mode) but with the addition of a narrow bandpass filter centered at 689.3 nm (ZET690/10x, Chroma). Spectrally resolved single-molecule imaging was then performed with Path 2 in the Spectrum Mode without the narrow bandpass filter, so that the undispersed images and the dispersed spectra of the same single molecules were simultaneously recorded through Path 1 and Path 2, respectively. 30,000-80,000 frames of images were typically recorded to generate the final SRM image, which, after analysis (below), enabled the determination of the positions and spectra of ~10$^6$ single molecules within minutes. Increased number of frames would lead to more single-molecule spectra at the expense of longer imaging time.

Acquired/recorded data were first split into two movies, each of which comprised a series of images obtained by Path 1 and Path 2, respectively. Single-molecule images were super-localized in 2D or 3D. The super-localized positions of single molecules in the initial short movies were used to map the coordinates of Path 1 and Path 2 via two different approaches that led to similar results.

In a first approach, the initial short movie was recorded with Path 2 being in the Image Mode. To analyze the subsequent spectral measurement data, the super-localized positions of single molecules in Path 1 were first projected to the coordinates of the Image Mode of Path 2 based on mapping functions generated from the initial short movie, and the resultant positions were projected again from the coordinates of Image Mode of Path 2 to the coordinates of the Spectrum Mode of Path 2 for a fixed wavelength (700 nm) basing on the aforementioned calibration results obtained via fluorescent beads.

In an alternative approach, the initial short movie was recorded with Path 2 in the Spectrum Mode with a narrow bandpass filter centered at 689.3 nm. To analyze the subsequent spectral measurement data, the super-localized positions of single molecules in Path 1 were projected to the coordinates of the Spectrum Mode of Path 2 for the fixed wavelength of 689.3 nm based on mapping functions generated from the initial short movie. The spectrum of each molecule was obtained based on the mapped position of either 700 nm or 689.3 nm emission in the Spectrum Mode of Path 2 and a spectral calibration curve. Overlapping spectra were rejected. For molecules that lasted for more than one frame, the super-localized positions and measured spectra in consecutive frames were combined. The spectral mean of each molecule is calculated through the intensity-weighted averaging of wavelength for the measured single-molecule spectrum and presented on a continuous color scale to generate "true-color" SRM images. For categorization of each molecule when the spectra of all dyes in the sample were known (either from separate measurements or from target-averaging), the measured spectrum of a single molecule was compared with the spectrum of each known dye by calculating the Pearson product-moment correlation coefficient for the intensity-wavelength relationship. The single molecule was then assigned to the dye that resulted in the highest correlation coefficient.

FIG. 4A, FIG. 4B and FIG. 5A, FIG. 5B show actual data obtained on a prototype based on the dual-objective system 10 of FIG. 1, with a small area of the raw data of single-molecule images and single-molecule spectra obtained for the same region of sample 14 in two camera frames separated in time.

The image of path 1 (FIG. 4A, image mode) and spectra of Path 2 (FIG. 4B, spectrum mode) of single AF647 molecules were simultaneously acquired (acquired in 9 ms) and shown in one camera frame. FIG. 5A and FIG. 5B show images/spectra from the same setup as FIG. 4A and FIG. 4B, but for another frame that is 1s later. The crosses in FIG. 4B and FIG. 5B are mapped spectral positions of 647 nm and 750 nm for each molecule.

Figure 6:
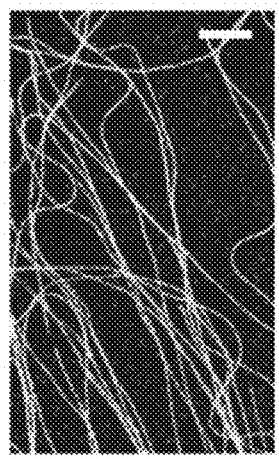
FIG. 6 shows a STORM/(F)PALM-type SRM image of the same area obtained through the system of FIG. 1.

FIG. 6 shows a STORM/(F)PALM-type SRM image of the same area described above for FIG. 4A and FIG. 4B. The image of FIG. 6 was constructed from 30 k frames of single-molecule images and super-localized positions of single molecules obtained through Path 1 of the system 10 of FIG. 1.

Figure 7:
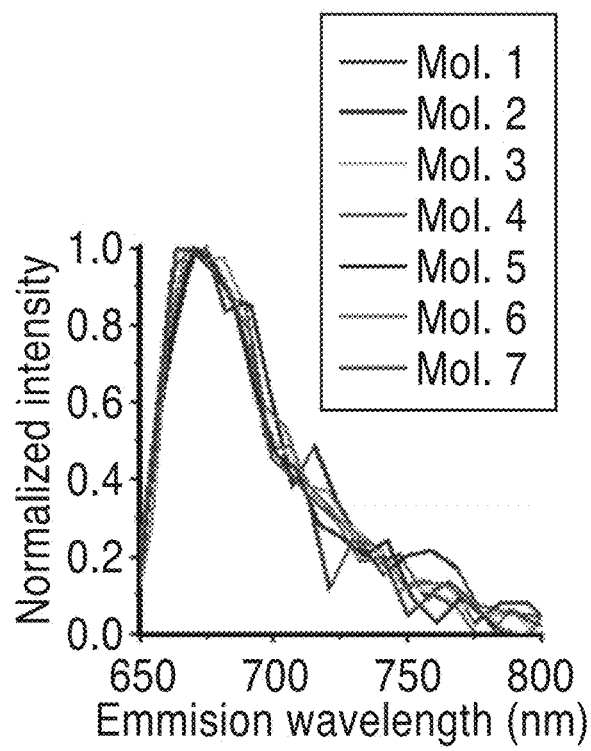
FIG. 7 is a plot of measured spectra of the 7 molecules in FIG. 4A and FIG. 4B.

Meanwhile, by mapping the localized positions of single molecules from Path 1 to the spectrum data of Path 2, the spectral positions of different wavelengths was determined for every molecule (cross marks in FIG. 4 B and FIG. 5B) and a calibrated spectrum for each molecule was obtained, as demonstrated in FIG. 7, showing a plot of measured spectra of the 7 molecules in FIG. 4A and FIG. 4B.

By matching the photoswitching rate to the EM-CCD camera 12 frame rate (110 FPS), the positions and spectra of millions of single molecules were concurrently obtained over the full camera frame in <10 minutes, thus demonstrating ultrahigh-throughput single-molecule spectral measurement.

The exceptionally large number of single-molecule spectra obtained with SR-STORM allowed for a statistical examination of how different molecules in the sample behave.

Figure 8:
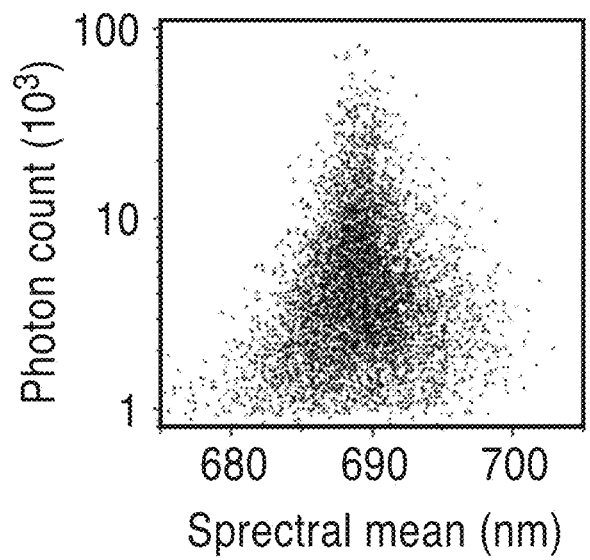
FIG. 8 is a plot of the measured spectral mean of single molecules vs. the detected photon count of each molecule for 6,406 molecules detected across the camera in a 3 second timeframe.

One unexpected result from ultrahigh-throughput single-molecule spectral measurement is that single molecules of the same dye exhibit very similar spectra. To facilitate a direct comparison of the emission wavelength of millions of single molecules, the spectral mean of each single molecule was calculated as the intensity-weighted average of wavelength. A small standard deviation of 2.6 nm was observed in spectral mean for 573, 527 molecules detected over 4.5 min in the sample 14. Such results are reflected in FIG. 8, which shows a plot of the measured spectral mean of single molecules vs. the detected photon count of each molecule for 6,406 molecules detected across the camera 12 in a 3 second timeframe. Larger variations were noted for dimmer molecules, attributable to lower signal-to-noise ratios.

Figure 9:
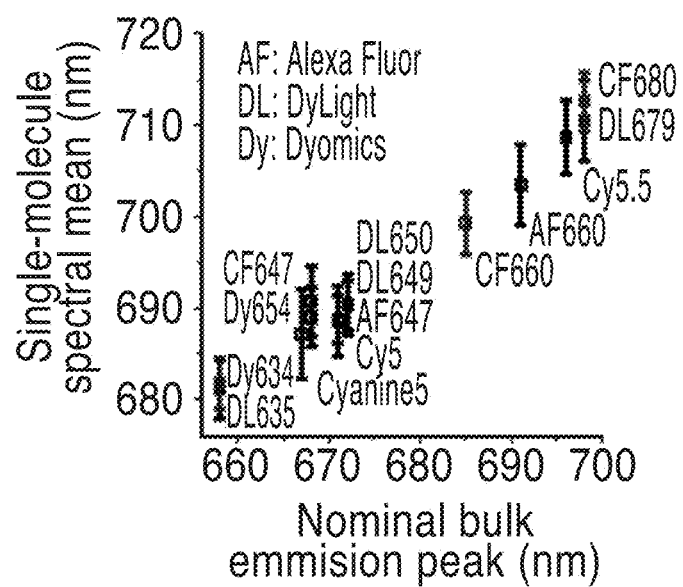
FIG. 9 is a plot of the measured spectral mean positions for single molecules of 14 different far-red dyes. Error bars represent standard deviation between single molecules.

At the same time, the brighter molecules (>10,000 detected photons) converged to an extremely small standard deviation of 1.4 nm. Overall, very small standard deviations (2.5 nm-4.5 nm) were found for the spectral mean between different single molecules for the 14 far-red dyes that were investigated. FIG. 9 is a plot of the measured spectral mean positions for single molecules of the 14 different far-red dyes. Error bars represent standard deviation between single molecules This result suggests that by directly resolving the spectrum of every molecule, the systems and methods of the present description can reliably distinguish single molecules of different dyes that differ minimally in emission spectrum. Such capability is harnessed in spectrally resolved super-resolution microscopy, as described below.

A noticeable advantage of the wide-field spectroscopy systems and methods of the present technology is high throughput. Using a camera, the spectra of tens to hundreds of point sources (single molecules) are simultaneously collected in the wide-field in a snapshot. All pixels of the camera are utilized, and modern EM-CCD cameras achieve >90% photon detection efficiency while offering 100+ FPS (frame per second) frame rates at 512×256 pixels. Thus, single-molecule spectral measurement of the entire field only takes <10 ms. In comparison, the traditional single-point approach necessitates point-by-point scanning of every pixel, and so the required time to sample a 2D field increases drastically (e.g. 100×100 steps×20 ms=200 s).

A notable feature of the systems and methods of the present technology is that the fluorescence spectra and positions of millions of single molecules are synchronously obtained. By integrating these results, a novel, spectrally resolved, "true-color" super-resolution microscopy is achieved, as opposed to previous multicolor STORM/(F) PALM approaches where each detected molecule is assigned to one of the labeled dyes and accordingly "false-colored."

Figure 10:
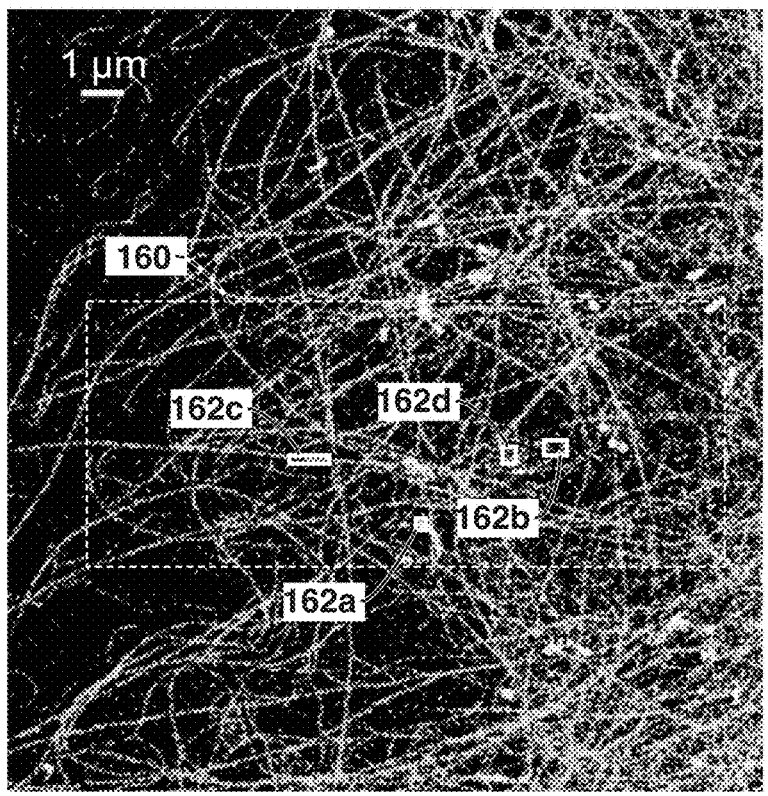
FIG. 10 shows a spectrally resolved SRM image of 4 different subcellular targets that were labeled by four far-red dyes at 10 nm spectral separation.
Figure 11A:
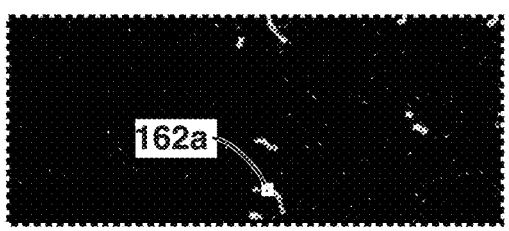
FIG. 11A through FIG. 11D show images of the separation of the four color channels for the dashed boxed area shown in FIG. 10, illustrating negligible misidentification (crosstalk) and excellent resolution for every channel.
Figure 11B:
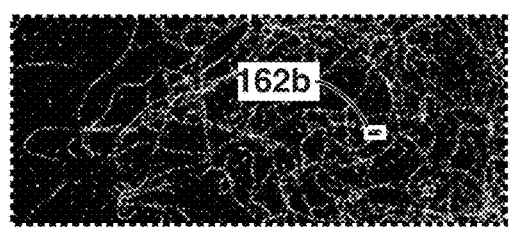
Figure 11C:
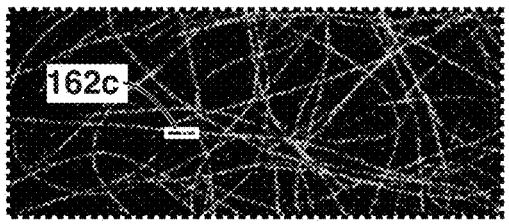
Figure 11D:
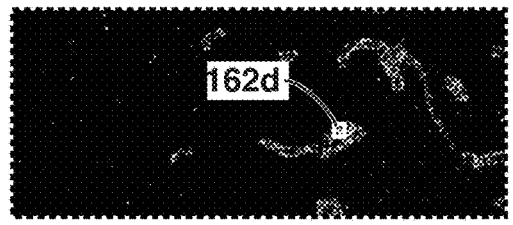
Figure 12:
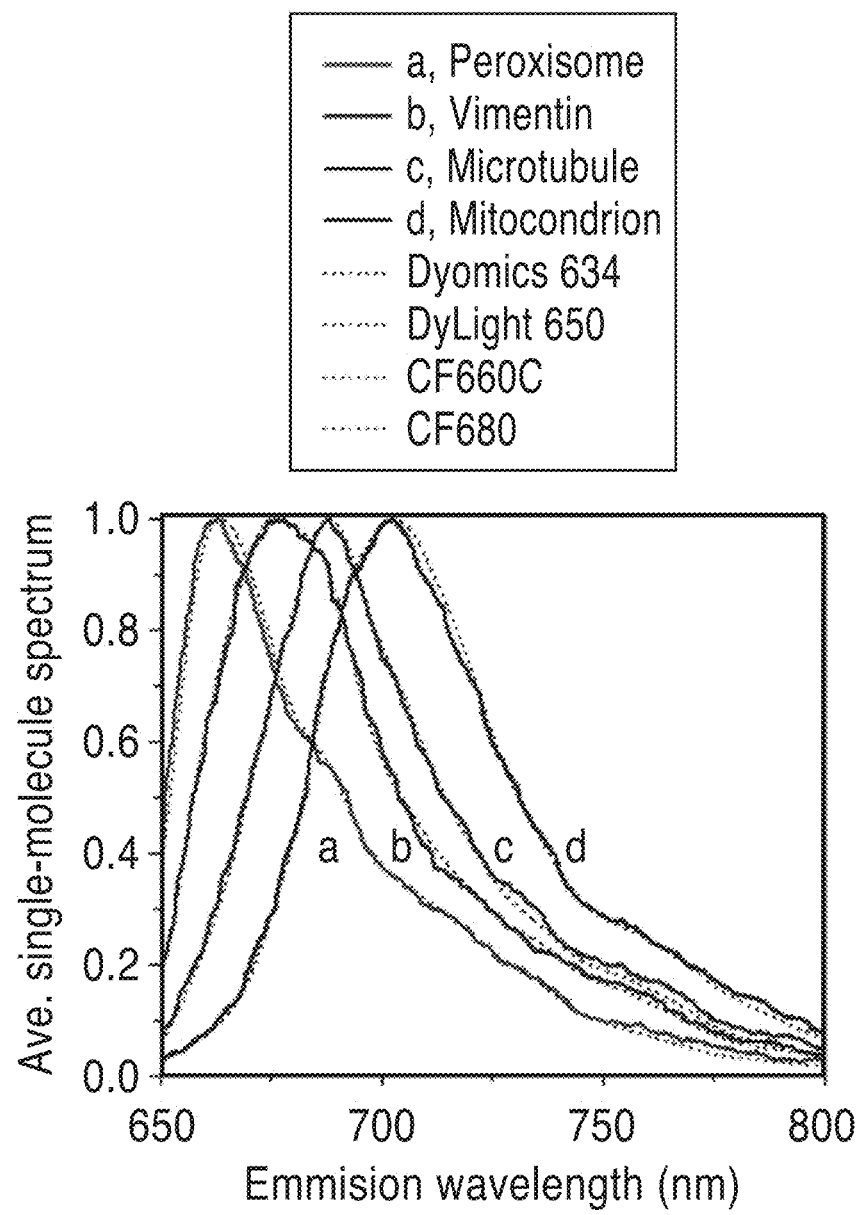
FIG. 12 shows a plot of the averaged single-molecule spectra for different subcellular structures in the solid smaller white boxes of FIG. 10, in comparison to the separately measured averaged single-molecule spectra of the four dyes used in the sample.

FIG. 10 through FIG. 12 demonstrate spectrally resolved super-resolution microscopy in which four far-red dyes that are only 10 nm apart in emission spectrum are used to densely label four distinct subcellular structures. To present both the spatial and spectral information of all (~106) measured single molecules, the position of each molecule in xy is plotted, and use a continuous color scale to denote the measured spectral mean of each molecule.

FIG. 10 shows a spectrally resolved SRM image of 4 different subcellular targets that were labeled by four far-red dyes at 10 nm spectral separation. Remarkably, molecules of different dyes are readily distinguishable in the novel "true-color" SRM images obtained using the systems and methods of the present technology, so that distinct colors (e.g., purple, cyan, green, and yellow, etc.) are observed for the differently labeled structures of mitochondria, microtubules, vimentin filaments, and peroxisomes, (marked as small white boxes 162a through 162d within dashed box 160), without a priori knowledge of the actual spectra of the dyes.

FIG. 11A through FIG. 11D show four separate images of the separation of the four color channels for the dashed-boxed area 160 shown in FIG. 10, illustrating negligible misidentification (crosstalk) and excellent resolution for every channel. Averaging the single-molecule spectra for each labeled, sub-diffraction-limit structure showed good agreement with the separately obtained single-molecule spectra of its corresponding dye. FIG. 12 shows a plot of the averaged single-molecule spectra (detailed as a through d for each of boxes 162a through 162d in FIG. 11A through FIG. 11D, respectively) for different subcellular structures in the white boxes of FIG. 10 in comparison to the separately measured averaged single-molecule spectra of the four dyes used in the sample.

5. System Implementation

Figure 13:
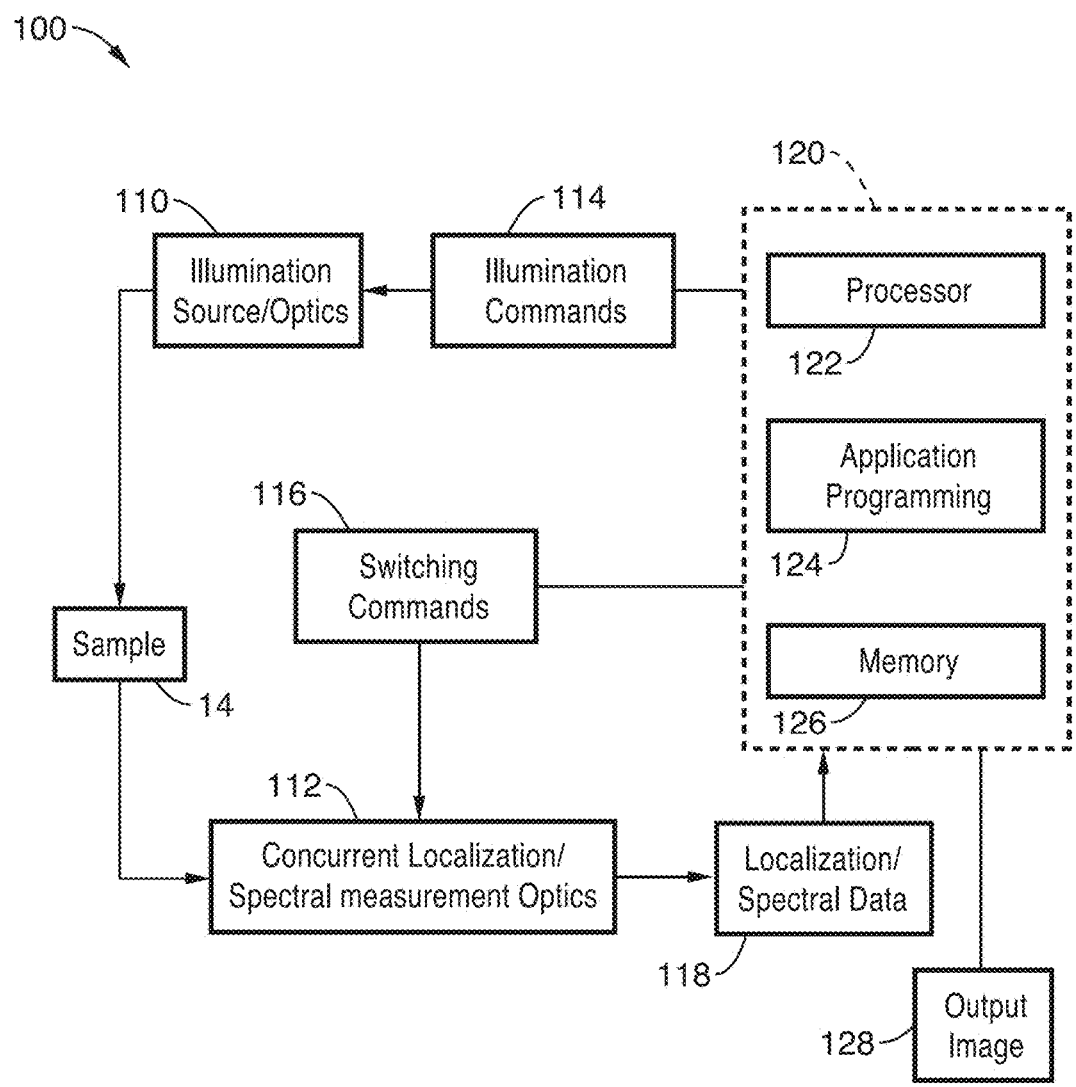
FIG. 13 shows a high-level schematic diagram of an acquisition system for concurrent spectral measurement and localization of single molecules in wide-field.

FIG. 13 shows a high-level system diagram of an acquisition system 100 for concurrent spectral measurement and localization of single molecules in wide-field. System 100 may incorporate the optical setup of either of imaging systems 10, 60 detailed in FIG. 1 and FIG. 2 as the concurrent localization and spectral measurement optics 112 to acquire localization and spectral data 118 of the sample 14. It is also appreciated that optics 112 may comprise any combination of components used in system 10 or system 60, or any optical setup configured to generate Path 1 and Path 2 for simultaneous localization and spectral data acquisition. Acquisition system 100 further includes a computer or computing device 120 including application programming 124 comprising instructions stored in memory 126 and operable on processor 122 for various control and/or data acquisition and processing operations with respect to the system. For example, programming 124 may comprise illumination commands 114 for operating the illumination source optics 110 at the sample 14 (e.g. for controlled photoswitching between dark and fluorescent states), as well as timing commands 116 for controlling optics 112 (e.g. control of stage 44 (FIG. 1) so optics (e.g. prism 45, mirrors 48) can be translated to switch Path 2 between the image mode and the spectrum mode). Application programming may further include instructions for processing the acquired localization/spectral measurement data 118 and outputting SRM images 128, such as, but not limited to, images such as the STORM/(F)PALM-type SRM image shown in FIG. 6, or any of the images shown in FIG. 4A through FIG. 5B, and FIG. 10 through 11D.

The systems and methods of the present technology are also readily applicable to 3D SRM. By introducing astigmatism into Path 1 via a cylindrical lens, 3D localization of single molecules is achieved. Meanwhile, the spectral information from Path 2 is not affected. Combining the 1D spectral and 3D spatial information obtained for each molecule thus results in rich information in four dimensions. The obtained single-molecule spectra again allows for "true-color" SRM and negligible misidentification between four color channels, but here each molecule is localized in 3D.

Similar spatial resolution of ~10 nm in the lateral directions and ~20 nm in the axial direction were achieved for all dyes. Virtual cross-sections in the xy-plane and yz-plane clearly show the relative 3D positions of the four sub-diffraction-limit structures. To further verify that the 3D SRM images of different dyes are aligned with each other in 3D, TOM20, a mitochondrial outer membrane protein, and ATP synthase, which should reside within mitochondria, were labeled with CF680 and AF647, respectively. As expected, virtual cross sections showed that the AF647 localizations were fully enclosed by CF680 localizations.

Besides enabling the acquisition of single-molecule fluorescence spectra in dense cell samples with exceptionally high throughput, the capability of the systems and methods of the present technology to obtain 3D SRM images while reliably distinguishing fluorophores that are similar in emission spectrum provides notable advantages. Substantial differences in STORM/(F)PALM performance are found for fluorophores that differ significantly in spectrum, and to date, dyes with the best performance cluster in the far-red range.

Sequential multicolor STORM/(F)PALM works with ~100 nm spectral separation; fluorophores of inferior performance are employed, and color crosstalk of <8% is achieved. Split-channel, ratiometric methods work for ~20 nm spectral separation at the expense of higher crosstalk (~20% for four-color imaging).

Activation-based multicolor STORM uses a single reporter dye but is limited by heavy crosstalk (10-20%). We achieved unambiguous (<2% crosstalk) identification of four far-red dyes at 10 nm spectral separation, and excellent SRM performance was observed for all dyes. Moreover, as a single optical path is used to localize all molecules, the 3D positions of different molecules are directly obtained in the same coordinates, thus circumventing the major challenges of aligning different color channels in 3D, as faced by approaches where multiple optical paths or filter sets are employed for localization.

Beyond what has already been demonstrated in the data presented herein, the systems and methods of the present technology would also allow for simultaneous SRM imaging of infinite number of dyes that are minimally different in emission spectrum. In addition, by employing fluorescent probes that are responsive to local environments, the systems and methods of the present technology can also enable chemical imaging at single-molecule and super-resolution levels to report on physical and chemical processes, e.g., polarity, pH, and concentration of specific chemicals, at nanometer-resolution.

The systems and methods of the present technology are particularly suited for, but not limited to, the following applications:

(a) Multicolor, 3D super-resolution microscopy: exhibiting excellent resolution, zero color crosstalk, and automatically aligned 3D images for 4+ color channels.

(b) Ultra-high throughput single-molecule spectroscopy: configured to obtain the fluorescence spectrum of millions of single molecules in a densely labeled sample in a few minutes.

(c) Chemical imaging with nanometer-resolution: identification of minor changes in the fluorescence spectra of single molecules in dense samples due to do variation in local environments.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. A wide-field spectroscopy method, comprising: imaging a molecule at a target location in a sample; and dispersing fluorescence of the molecule directly in the wide-field.

2. The method of any preceding embodiment, further comprising performing concurrent spectral measurement and localization of the molecule in wide-field.

3. The method of any preceding embodiment, further comprising: imaging the molecule using a single objective and splitting the fluorescence into two paths for concurrent spectral measurement and localization of the molecule in wide-field.

4. The method of any preceding embodiment, further comprising: simultaneously imaging the molecule with two objectives to acquire first and second images of the molecule; and using the first image to determine the position of the molecule at the target location; and using the second image to generate spectra of the molecule in wide-field.

5. A system for spectrally resolved super-resolution microscopy, comprising: (a) a computer processor; and (b) a non-transitory computer-readable memory storing instructions executable by the computer processor; (c) wherein said instructions, when executed by the computer processor, perform steps comprising: (i) illuminating a sample comprising a plurality of molecules; (ii) generating a non-dispersed wide-field image of a molecule within the sample; and (iii) simultaneously dispersing fluorescence of the molecule to concurrently acquire spectral data and location data of the molecule in wide-field within the image.

6. The system of any preceding embodiment, wherein illuminating the sample comprises stochastic switching of the molecules from a non-emitting dark state and an emitting fluorescent state for synchronous spectrum measurement and localization of the plurality of molecules.

7. The system of any preceding embodiment: wherein illuminating the sample comprises illuminating the sample such that a first subset of the molecules are placed into the non-emitting dark state and a smaller, sparsely-distributed second subset of the molecules are placed into the emitting fluorescent state such that the fluorescence of the second subset of emitting molecules is dispersed into non-overlapping spectra in wide-field.

8. The system of any preceding embodiment, wherein the spectral data and location data are acquired at a throughput rate of at least ten thousand of molecules per second.

9. The system of any preceding embodiment, said instructions when executed by the computer processor further perform steps comprising: constructing a spectrally-resolved, stochastic optical reconstruction microscopy (SR-STORM) super-resolution image of the sample from a plurality of single-molecule images and localized positions of single molecules.

10. The system of any preceding embodiment, said instructions when executed by the computer processor further perform steps comprising: simultaneously imaging the sample in a first path and a second path; wherein the first path is configured to generate a first image comprising the non-dispersed wide-field image of the molecule; and wherein the second path is configured to generate a second image comprising the dispersed spectral data of the molecule in wide-field.

11. The system of any preceding embodiment, said instructions when executed by the computer processor further perform steps comprising: simultaneously detecting the first image and second image on a single wide-field image frame.

12. The system of any preceding embodiment, said instructions when executed by the computer processor further perform steps comprising: mapping localized positions of single molecules acquired from the first path to spectrum data acquired from the second path.

13. The system of any preceding embodiment, said instructions when executed by the computer processor further perform steps comprising: calculating spectral positions of different wavelengths for each molecule.

14. The system of any preceding embodiment, said instructions when executed by the computer processor further perform steps comprising: generating a calibrated spectrum for each molecule.

15. The system of any preceding embodiment, further comprising: at least one optical element directed at the sample and disposed within the first path and the second path for generating the first and second images; and a detector disposed within the first path and the second path for receiving the first and second images.

16. The system of any preceding embodiment, wherein the at least one optical element comprises: a first objective; and a beam splitter in an optical path the first objective for splitting the optical path into the first path and the second path.

17. The system of any preceding embodiment, wherein the at least one optical element comprises: a first objective and a second objective at opposing ends of the sample; and wherein the first objective is configured to generate the first path and the second objective is configured to generate the second path.

18. The system of any preceding embodiment, further comprising an illumination source for illuminating the sample; wherein illuminating the sample comprises stochastic switching of the molecules from a non-emitting dark state and an emitting fluorescent state for synchronous spectrum measurement and localization of the plurality of molecules.

19. The system of any preceding embodiment: wherein the detector comprises a camera having a frame rate; and wherein stochastic switching of the molecules from a non-emitting dark state and an emitting fluorescent state is switched off at a rate configured to substantially match the frame rate of the camera.

20. The system of any preceding embodiment, wherein stochastic switching of the molecules from a non-emitting dark state and an emitting fluorescent state is switched on at a rate configured to achieve an optimal density of emitting molecules.

21. The system of any preceding embodiment, wherein the second path comprises: an image mode and a spectrum mode; and a stage disposed within the second path to switch from the image mode to the spectrum mode; wherein said instructions are further configured for controlling translation of the stage from the image mode to the spectrum mode.

22. The system of any preceding embodiment: the stage further comprising a prism and two relay lenses within the second optical path; and wherein prism is positioned in a Fourier plane of the two relay lenses for dispersing spectra within the second image in the spectrum mode.

23. A method for spectrally resolved super-resolution microscopy, comprising: illuminating a sample comprising a plurality of molecules; generating a non-dispersed wide-field image of a molecule within the sample; and simultaneously dispersing fluorescence of the molecule to concurrently acquire spectral data and location data of the molecule in wide-field within the image.

24. The method of any preceding embodiment, wherein illuminating the sample comprises stochastic switching of the molecules from a non-emitting dark state and an emitting fluorescent state for synchronous spectrum measurement and localization of the plurality of molecules.

25. The method of any preceding embodiment: wherein illuminating the sample comprises illuminating the sample such that a first subset of the molecules are placed into the non-emitting dark state and a smaller, sparsely-distributed second subset of the molecules are placed into the emitting fluorescent state such that the fluorescence of the second subset of emitting molecules is dispersed into non-overlapping spectra in wide-field.

26. The method of any preceding embodiment, wherein the spectral data and location data are acquired at a throughput rate of at least ten thousand of molecules per second.

27. The method of any preceding embodiment, further comprising: constructing a spectrally-resolved, stochastic optical reconstruction microscopy (SR-STORM) super-resolution image of the sample from a plurality of single-molecule images and localized positions of single molecules.

28. The method of any preceding embodiment, further comprising: simultaneously imaging the sample in a first path and a second path; wherein the first path is configured to generate a first image comprising the non-dispersed wide-field image of the molecule; and wherein the second path is configured to generate a second image comprising the dispersed spectral data of the molecule in wide-field.

29. The method of any preceding embodiment, further comprising: simultaneously detecting the first image and second image on a single wide-field image frame.

30. The method of any preceding embodiment, further comprising: mapping localized positions of single molecules acquired from the first path to spectrum data acquired from the second path.

31. The method of any preceding embodiment, further comprising: calculating spectral positions of different wavelengths for each molecule.

32. The method of any preceding embodiment, further comprising: generating a calibrated spectrum for each molecule.

33. The method of any preceding embodiment: wherein imaging of the sample is acquired with a camera having a frame rate; wherein illuminating the sample comprises stochastic switching of the molecules from a non-emitting dark state and an emitting fluorescent state for synchronous spectrum measurement and localization of the plurality of molecules; and wherein stochastic switching of the molecules from a non-emitting dark state and an emitting fluorescent state is switched off at a rate configured to substantially match the frame rate of the camera.

34. The method of any preceding embodiment, wherein stochastic switching of the molecules from a non-emitting dark state and an emitting fluorescent state is switched on at a rate configured to achieve an optimal density of emitting molecules.

35. The method of any preceding embodiment, wherein the second path comprises an image mode and a spectrum mode for dispersing spectra within the second image, the method further comprising: switching the second path from the image mode to the spectrum mode.

36. An apparatus for spectrally resolved super-resolution microscopy, comprising: at least one optical element directed at a sample comprising a plurality of molecules; an illumination source configured for illuminating the sample; wherein the at least one optical element is configured to comprise a first path and a second path; wherein the first path is configured to generate a first image comprising a non-dispersed wide-field image of a molecule within the sample; and wherein the second path is configured to concurrently generate a second image comprising dispersed spectral data of the molecule in wide-field; and a detector coupled to the first path and the second path for receiving the first and second images to concurrently acquire spectral data and location data of the molecule in wide-field within the image.

37. The apparatus of any preceding embodiment, wherein the at least one optical element comprises: a first objective; and a beam splitter in an optical path the first objective for splitting the optical path into the first path and the second path.

38. The apparatus of any preceding embodiment, wherein the at least one optical element comprises: a first objective and a second objective at opposing ends of the sample; and wherein the first objective is configured to generate the first path and the second objective is configured to generate the second path.

39. The apparatus of any preceding embodiment, further comprising an illumination source for illuminating the sample; wherein the illumination source is configured to illuminate the sample via stochastic switching of the molecules from a non-emitting dark state and an emitting fluorescent state for synchronous spectrum measurement and localization of the plurality of molecules.

40. The apparatus of any preceding embodiment: wherein the detector comprises a camera having a frame rate; and wherein stochastic switching of the molecules from a non-emitting dark state and an emitting fluorescent state is switched off at a rate configured to substantially match the frame rate of the camera.

41. The apparatus of any preceding embodiment, wherein the second path comprises: an image mode and a spectrum mode; and a stage disposed within the second path to switch from the image mode to the spectrum mode; wherein said instructions are further configured for controlling translation of the stage from the image mode to the spectrum mode.

42. The apparatus of any preceding embodiment: the stage further comprising a prism and two relay lenses within the second optical path; and wherein prism is positioned in a Fourier plane of the two relay lenses for dispersing spectra within the second image in the spectrum mode.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for spectrally resolved super-resolution microscopy, comprising:
   (a) a computer processor; and
   (b) a non-transitory computer-readable memory storing instructions executable by the computer processor;
   (c) wherein said instructions, when executed by the computer processor, perform steps comprising:
      (i) illuminating a sample comprising a plurality of molecules;
      (ii) generating a non-dispersed wide-field image of a molecule within the sample; and
      (iii) simultaneously dispersing fluorescence of the molecule to concurrently acquire spectral data and location data of the molecule in wide-field within the image.

2. The system of claim 1, wherein illuminating the sample comprises stochastic switching of the molecules from a non-emitting dark state and an emitting fluorescent state for synchronous spectrum measurement and localization of the plurality of molecules.

3. The system of claim 2:
   wherein illuminating the sample comprises illuminating the sample such that a first subset of the molecules are placed into the non-emitting dark state and a smaller, sparsely-distributed second subset of the molecules are placed into the emitting fluorescent state such that the fluorescence of the second subset of emitting molecules is dispersed into non-overlapping spectra in wide-field.

4. The system of claim 2, wherein the spectral data and location data are acquired at a throughput rate of at least ten thousand of molecules per second.

5. The system of claim 1, said instructions when executed by the computer processor further perform steps comprising:
   constructing a spectrally-resolved, stochastic optical reconstruction microscopy (SR-STORM) super-resolution image of the sample from a plurality of single-molecule images and localized positions of single molecules.

6. The system of claim 1, said instructions when executed by the computer processor further perform steps comprising:
   simultaneously imaging the sample in a first path and a second path;
   wherein the first path is configured to generate a first image comprising the non-dispersed wide-field image of the molecule; and
   wherein the second path is configured to generate a second image comprising the dispersed spectral data of the molecule in wide-field.

7. The system of claim 6, said instructions when executed by the computer processor further perform steps comprising:
   simultaneously detecting the first image and second image on a single wide-field image frame.

8. The system of claim 6, said instructions when executed by the computer processor further perform steps comprising:
   mapping localized positions of single molecules acquired from the first path to spectrum data acquired from the second path.

9. The system of claim 8, said instructions when executed by the computer processor further perform steps comprising:
   calculating spectral positions of different wavelengths for each molecule.

10. The system of claim 8, said instructions when executed by the computer processor further perform steps comprising:
    generating a calibrated spectrum for each molecule.

11. The system of claim 6, further comprising:
    at least one optical element directed at the sample and disposed within the first path and the second path for generating the first and second images; and
    a detector disposed within the first path and the second path for receiving the first and second images.

12. The system of claim 11, wherein the at least one optical element comprises:
    a first objective; and
    a beam splitter in an optical path the first objective for splitting the optical path into the first path and the second path.

13. The system of claim 11, wherein the at least one optical element comprises:
    a first objective and a second objective at opposing ends of the sample; and
    wherein the first objective is configured to generate the first path and the second objective is configured to generate the second path.

14. The system of claim 11, further comprising an illumination source for illuminating the sample;
    wherein illuminating the sample comprises stochastic switching of the molecules from a non-emitting dark state and an emitting fluorescent state for synchronous spectrum measurement and localization of the plurality of molecules.

15. The system of claim 14:
    wherein the detector comprises a camera having a frame rate; and
    wherein stochastic switching of the molecules from a non-emitting dark state and an emitting fluorescent state is switched off at a rate configured to substantially match the frame rate of the camera.

16. The system of claim 15, wherein stochastic switching of the molecules from a non-emitting dark state and an emitting fluorescent state is switched on at a rate configured to achieve an optimal density of emitting molecules.

17. The system of claim 11, wherein the second path comprises:
    an image mode and a spectrum mode; and
    a stage disposed within the second path to switch from the image mode to the spectrum mode;

wherein said instructions are further configured for controlling translation of the stage from the image mode to the spectrum mode.

18. The system of claim 17:
the stage further comprising a prism and two relay lenses within the second optical path; and
wherein prism is positioned in a Fourier plane of the two relay lenses for dispersing spectra within the second image in the spectrum mode.

19. A method for spectrally resolved super-resolution microscopy, comprising:
illuminating a sample comprising a plurality of molecules;
generating a non-dispersed wide-field image of a molecule within the sample; and
simultaneously dispersing fluorescence of the molecule to concurrently acquire spectral data and location data of the molecule in wide-field within the image.

20. The method of claim 19, wherein illuminating the sample comprises stochastic switching of the molecules from a non-emitting dark state and an emitting fluorescent state for synchronous spectrum measurement and localization of the plurality of molecules.

21. The method of claim 20:
wherein illuminating the sample comprises illuminating the sample such that a first subset of the molecules are placed into the non-emitting dark state and a smaller, sparsely-distributed second subset of the molecules are placed into the emitting fluorescent state such that the fluorescence of the second subset of emitting molecules is dispersed into non-overlapping spectra in wide-field.

22. The method of claim 20, wherein the spectral data and location data are acquired at a throughput rate of at least ten thousand of molecules per second.

23. The method of claim 19, further comprising:
constructing a spectrally-resolved, stochastic optical reconstruction microscopy (SR-STORM) super-resolution image of the sample from a plurality of single-molecule images and localized positions of single molecules.

24. The method of claim 19, further comprising:
simultaneously imaging the sample in a first path and a second path;
wherein the first path is configured to generate a first image comprising the non-dispersed wide-field image of the molecule; and
wherein the second path is configured to generate a second image comprising the dispersed spectral data of the molecule in wide-field.

25. The method of claim 24, further comprising:
simultaneously detecting the first image and second image on a single wide-field image frame.

26. The method of claim 24, further comprising:
mapping localized positions of single molecules acquired from the first path to spectrum data acquired from the second path.

27. The method of claim 26, further comprising:
calculating spectral positions of different wavelengths for each molecule.

28. The method of claim 26, further comprising:
generating a calibrated spectrum for each molecule.

29. The method of claim 24:
wherein imaging of the sample is acquired with a camera having a frame rate; and
wherein illuminating the sample comprises stochastic switching of the molecules from a non-emitting dark state and an emitting fluorescent state for synchronous spectrum measurement and localization of the plurality of molecules; and
wherein stochastic switching of the molecules from a non-emitting dark state and an emitting fluorescent state is switched off at a rate configured to substantially match the frame rate of the camera.

30. The method of claim 29, wherein stochastic switching of the molecules from a non-emitting dark state and an emitting fluorescent state is switched on at a rate configured to achieve an optimal density of emitting molecules.

31. The method of claim 24, wherein the second path comprises an image mode and a spectrum mode for dispersing spectra within the second image, the method further comprising:
switching the second path from the image mode to the spectrum mode.

32. An apparatus for spectrally resolved super-resolution microscopy, comprising:
at least one optical element directed at a sample comprising a plurality of molecules;
an illumination source configured for illuminating the sample;
wherein the at least one optical element is configured to comprise a first path and a second path;
wherein the first path is configured to generate a first image comprising a non-dispersed wide-field image of a molecule within the sample; and
wherein the second path is configured to concurrently generate a second image comprising dispersed spectral data of the molecule in wide-field; and
a detector coupled to the first path and the second path for receiving the first and second images to concurrently acquire spectral data and location data of the molecule in wide-field within the image.

33. The apparatus of claim 32, wherein the at least one optical element comprises:
a first objective; and
a beam splitter in an optical path the first objective for splitting the optical path into the first path and the second path.

34. The apparatus of claim 32, wherein the at least one optical element comprises:
a first objective and a second objective at opposing ends of the sample; and
wherein the first objective is configured to generate the first path and the second objective is configured to generate the second path.

35. The apparatus of claim 32, further comprising an illumination source for illuminating the sample;
wherein the illumination source is configured to illuminate the sample via stochastic switching of the molecules from a non-emitting dark state and an emitting fluorescent state for synchronous spectrum measurement and localization of the plurality of molecules.

36. The apparatus of claim 35:
wherein the detector comprises a camera having a frame rate; and
wherein stochastic switching of the molecules from a non-emitting dark state and an emitting fluorescent state is switched off at a rate configured to substantially match the frame rate of the camera.

37. The apparatus of claim 32, wherein the second path comprises:
an image mode and a spectrum mode; and
a stage disposed within the second path to switch from the image mode to the spectrum mode;

wherein said instructions are further configured for controlling translation of the stage from the image mode to the spectrum mode.

38. The apparatus of claim 37:
the stage further comprising a prism and two relay lenses within the second optical path; and
wherein prism is positioned in a Fourier plane of the two relay lenses for dispersing spectra within the second image in the spectrum mode.

\* \* \* \* \*